US011357470B1

(12) United States Patent
Adithya et al.

(10) Patent No.: US 11,357,470 B1
(45) Date of Patent: Jun. 14, 2022

(54) SYSTEMS AND METHODS FOR IDENTIFYING A BIOMEDICAL CONDITION

(71) Applicant: University of South Florida, Tampa, FL (US)

(72) Inventors: Prashanth Chetlur Adithya, Cape Coral, FL (US); Shraddha Pandey, Tampa, FL (US); Ravi Sankar, Tampa, FL (US); Wilfrido Alejandro Moreno, Temple Terrace, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 16/430,368

(22) Filed: Jun. 3, 2019

Related U.S. Application Data

(60) Provisional application No. 62/679,235, filed on Jun. 1, 2018.

(51) Int. Cl.
*A61B 5/026* (2006.01)
*A61B 5/00* (2006.01)
*A61B 7/02* (2006.01)

(52) U.S. Cl.
CPC .............. *A61B 7/023* (2013.01); *A61B 5/026* (2013.01); *A61B 5/7203* (2013.01); *A61B 5/7264* (2013.01); *A61B 5/726* (2013.01); *A61B 5/7257* (2013.01)

(58) Field of Classification Search
CPC ........... A61B 5/0205; A61B 5/02; A61B 7/04; A61B 5/726; A61B 5/7203; A61B 5/7264
See application file for complete search history.

(56) References Cited

U.S. PATENT DOCUMENTS

| 6,178,261 | B1 | 1/2001 | Williams |  |
|---|---|---|---|---|
| 8,140,331 | B2 | 3/2012 | Lou |  |
| 9,198,634 | B2 * | 12/2015 | Pretorius | ................ A61B 5/349 |
| 10,667,701 | B1 | 6/2020 | Adithya |  |
| 2018/0042503 | A1 * | 2/2018 | Chauhan | ................ A61B 5/316 |

OTHER PUBLICATIONS

Adithya, P.C. et al., "A Novel Acoustic Catheter Stethoscope Based Acquisition and Signal Processing Framework to Extract Multiple Bio Signals," in Proc, 39th Annual International Conference of the IEEE Engineering in Medicine and Biology Society, Jeju, Korea, pp. 1336-1339, Jul. 2017.

(Continued)

*Primary Examiner* — Carl H Layno
*Assistant Examiner* — Aya Ziad Bakkar
(74) *Attorney, Agent, or Firm* — Quarles & Brady LLP

(57) ABSTRACT

In one embodiment, a system for identifying a biomedical condition of a subject includes apparatus for collecting blood flow sounds from the subject and a computing device that stores computer-executable instructions that are configured to: receive the collected blood flow sounds, extract acoustic heart pulses from the collected blood flow sounds, segment the acoustic heart pulses to obtain acoustic heart pulse segments, compute a continuous time wavelet transform-based feature for each acoustic heart pulse segment, and perform clustering on the computed continuous time wavelet transform-based features to determine whether or not the subject is experiencing the biomedical condition.

16 Claims, 4 Drawing Sheets

(56) References Cited

OTHER PUBLICATIONS

Adithya, P.C. et al., "Cluster Analysis Framework for Novel Acoustic Catheter Stethoscope," Proc. 2017 IEEE Healthcare Innovations and Point of Care Technologies (HI-POCT), pp. 22-25, Nov. 2017.

Ahlstrom, C. Processing of the Phonocardiographic Signal: methods for the intelligent stethoscope. Diss. Institutionen for medicinsk teknik, 2006.

Amit, G. et al., "Cluster Analysis and Classification of Heart Sounds," Biomedical Signal Processing and Control, vol. 4 No. 1, pp. 26-36, 2009.

Brandes, T. S.. "Feature vector selection and use with hidden Markov models to identify frequency-modulated bioacoustic signals amidst noise." IEEE Transactions on Audio, Speech, and Language Processing 16.6 (2008) 1173-1180.

Flores-Tapia, D. et al. "Heart Sound Cancellation Based on Multiscale Products and Linear Prediction," IEEE Transactions on Biomedical Engineering, vol. 54, No. 2, pp. 234-243, Feb. 2007.

Gupta, C.N. et al., "Segmentation and Classification of Heart Sounds," in Proc. Canadian Conference on Electrical and Computer Engineering, Saskatoon, pp. 1674-1677, May 2005.

Labate, D. et al., "Empirical Mode Decomposition vs. Wavelet Decomposition for the Extraction of Respiratory Signal from Single-Channel ECG: A Comparison," IEEE Sensors Journal, vol. 13, No. 7, pp. 2666-2674, Jul. 2013.

Phua, K., et al. "Heart sound as a biometric." Pattern Recognition 41.3 (2008): 906-919.

Romo-Vázquez, R. et al. "Blind Source Separation, Wavelet Denoising and Discriminant Analysis for EEG Artefacts and Noise Cancelling," Biomedical Signal Processing and Control, vol. 7, No. 4, pp. 389-400, Jul. 2012.

\* cited by examiner

SYSTEMS AND METHODS FOR IDENTIFYING A BIOMEDICAL CONDITION

CROSS-REFERENCE TO RELATED APPLICATION

This application claims priority to U.S. Provisional Application Ser. No. 62/679,235, filed Jun. 1, 2018, which is hereby incorporated by reference herein in its entirety.

BACKGROUND

The Centers for Disease Control and Prevention estimates that more than 600,000 people die of heart diseases every year in the United States. In light of the prevalence of heart disease, critical care units typically acquire blood pressure, heart, and respiratory rates among other vital biosignals to monitor for heart-related issues, including arrhythmia.

Traditional assessment methodologies use either an electrocardiogram- or a phonocardiogram-based feature extraction and pattern recognition framework for arrhythmia detection. Extensive research has been dedicated towards analysis of acoustic signals like heart sounds, respiratory sounds, and speech signals. Automated analysis of any acoustic signal includes noise cancellation, segmentation, feature extraction, cluster analysis, and/or classification. Noise cancellation and segmentation techniques are based on the objective of the clustering and/or classification. Studies in the literature have used standard features like mean, variance, zero crossing rate, time-frequency distribution, Fourier transform, Mel frequency cepstral coefficients, and linear predictive coding for representation of an acoustic signal. Clustering and/or classification techniques such as hierarchical, K-means clustering, K-nearest-neighbor, Gaussian-Bayes, and neural networks have been used in studies in conjunction with feature extraction to accomplish bioacoustic signal pattern recognition.

Despite the advancements in the data acquisition systems, signal processing, and artificial intelligence techniques, the monitoring techniques used by critical care units within the United States generate false positive indications of arrhythmia at a rate of around 90%. In view of this fact, it can be appreciated that it would be desirable to have a system and method that generate more accurate results.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it can be appreciated that it would be desirable to have a system and method for identifying a biomedical condition, such as arrhythmia, that yields more accurate results than the current techniques. Disclosed herein are examples of such systems and methods. In some embodiments, blood flow sounds of the subject are collected using an acoustic catheter stethoscope and are then preprocessed to extract acoustic heart pulses. The extracted acoustic heart pulses are then processed using a novel feature extraction and pattern recognition based machine learning framework that can be used to determine whether or not the subject is experiencing the biomedical condition. In some embodiments, the extracted features are multiscale energy (MSE) features and the pattern recognition is performed using a K-means clustering algorithm.

In the following disclosure, various specific embodiments are described. It is to be understood that those embodiments are example implementations of the disclosed inventions and that alternative embodiments are possible. All such embodiments are intended to fall within the scope of this disclosure.

Data Acquisition

Figure 1:
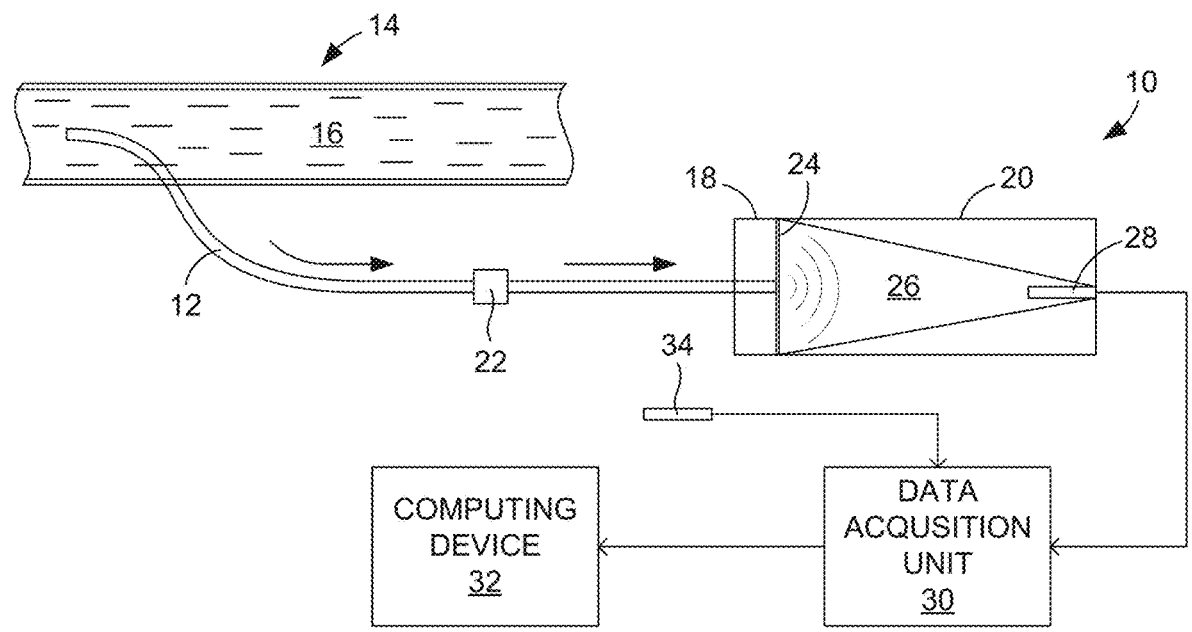
FIG. 1 is a schematic diagram of an embodiment of a system for identifying a biomedical condition.

FIG. 1 illustrates an embodiment of a system 10 for identifying a biomedical condition of a subject. The system 10 is configured to collect (acquire) data, in the form of bioacoustic signals, that can analyzed to identify the biomedical condition, which can be a condition associated with heart or pulmonary activity. In the disclosure that follows, it is assumed that the system 10 will be used to analyze acoustic heart pulses for the purpose of identifying the presence or absence of arrhythmia. While this specific application is discussed in detail in this disclosure as an example for purposes of discussion, it will be appreciated that this is just one application for the disclosed systems and methods. Not only can the system 10 be used to identify other cardiac conditions, it further can be used to identify non-cardiac conditions, such a respiratory conditions. Moreover, while a specific system 10 is illustrated in FIG. 1 and described in detail below, it will be appreciated that the apparatus that is used to collect the bioacoustic signals is not critical to the disclosed analysis. Instead, it is the processing of the collected signals that is of greater significance to this disclosure.

As shown in FIG. 1, the system 10 includes a catheter 12 comprising a flexible tube that is configured for insertion in a subject's blood vessel 14, such as an artery or vein. When so inserted, the distal end of the catheter 12 is immersed in the blood 16 that flows through the vessel 14. The proximal end of the catheter 12 is received by, and therefore connected to, a coupling member 18 that is, in turn, connected to a waveguide 20. In some embodiments, the coupling member 18 is mounted to the waveguide. As is also shown in FIG. 1, a port 22 can be provided along the length of the catheter 12 between its distal and proximal ends. When provided, this port 22 can be used to flush the catheter 12 with an appropriate fluid, such as saline.

Mounted to the coupling member 18 is a flexible barrier 24. This barrier 24 can be formed as a thin polymeric membrane that is on a first side in fluid communication with the blood delivered to the coupling member 18 by the catheter 12, and on a second side in fluid communication with air contained within an interior air chamber 26 of the waveguide 20. Blood flows from the venous or arterial vessel 14 through the catheter 12 and to the barrier 24, which halts the flow of blood and acts as a fluid-to-air coupler. At this boundary, the blood column oscillates due to changes in the stagnation pressure within the catheter 12, i.e., the frequency at which the blood is being pumped. The stagnation pressure that is impinged onto the barrier 24 induces a pressure field (in the form of pressure waves) that propagates along the air chamber 26 of the waveguide 20 from its distal end, at which the barrier 24 is located, to its proximal end, at which a first microphone 28 is located. By way of example, the first microphone 28 can comprise a condenser microphone, such as the GRAS 46 AD microphone. As shown in FIG. 1, the air chamber 26 can be conical and arranged such that the barrier 24 is located at its wide end and the first microphone 28 is located at its narrow end. In such a case, the acoustic pressure waves are focused on the first microphone 28 for maximal energy transfer.

The pressure field sensed by the first microphone 28 may be designated as the total pressure, $P_{total}$. According to the basic principles of fluid mechanics, $P_{total}$ is the sum of static pressure, $P_{static}$, and dynamic pressure, $P_{dynamic}$. $P_{static}$ results from intramolecular interaction and $P_{dynamic}$ results from the velocity of the blood flow. It was observed that the first microphone 28, which may be referred to as a pressure field microphone, partly cancels out the $P_{static}$ data from the acquired $P_{total}$ data through a static pressure equalization vent in the waveguide 20 (not shown) that was originally designed to equalize the effect of ambient pressure. Therefore, it was concluded that the acquired $P_{total}$ predominantly comprises pressure data corresponding to $P_{dynamic}$ with trace amounts of $P_{static}$. $P_{dynamic}$ can be used to identify both heart signals and respiratory signals.

The pressure field sensed by the first microphone 28 is transmitted to a data acquisition unit 30 as an analog acoustic pressure signal. The data acquisition unit 30 converts the analog acoustic pressure signal into a digital acoustic pressure signal that can then be transmitted to a computing device 32 for processing. An analog acoustic signal is also provided to the data acquisition unit 30 from a second microphone 34 that is positioned within the environment surrounding the subject for the purpose of collecting ambient noise that can be used for noise cancellation purposes. By way of example, the second microphone 34, which may be referred to as an acoustic microphone, can also comprise a condenser microphone, such as the GRAS 46 AE. As with the analog acoustic pressure signal from the first microphone 28, the analog acoustic signal from the second microphone 34 can be digitized by the data acquisition unit 30 and provided to the computing device 32 for processing.

As the system 10 includes a catheter 12 and a microphone 28 that are used to "listen" to acoustic heart signals (i.e., pulses) as one could with a stethoscope, the apparatus of the system used to collect the acoustic heart signals can be referred to as an "acoustic catheter stethoscope."

Figure 2:
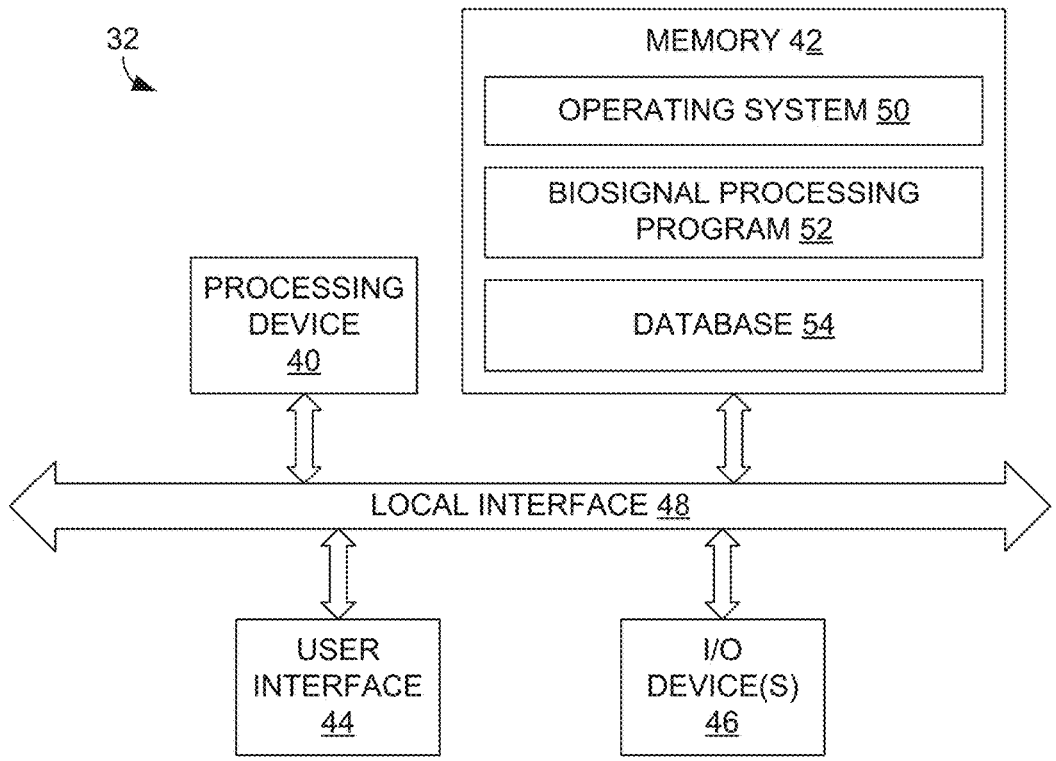
FIG. 2 is a block diagram of an embodiment of a computing device shown in FIG. 1.

FIG. 2 illustrates an example configuration for the computing device 32 shown in FIG. 1. Generally speaking, the computing device 32 can comprise any device that has the computing power to execute software programs necessary to perform the signal processing described below. Accordingly, the computing device 32 can be configured as a desktop computer, a notebook computer, a tablet computer, or a dedicated device configured solely for use in determining biomedical parameters from the pressure signals. Irrespective of its configuration, the computing device 32 generally includes a processing device 40, memory 42, one or more user interface devices 44, and one or more input/output devices 46, each of which is connected to a local interface 48.

The memory 42 (a non-transitory computer-readable medium) of the computing device 32 stores an operating system 50 and a biosignal processing system 52. The biosignal processing system 52 comprises one or more software programs that include one or more algorithms including computer-executable instructions that are configured to digitize acoustic pressure signals (i.e., blood flow sounds) received from the data acquisition unit 30 for the purpose identifying the biomedical condition. As described in greater detail below, the biosignal processing system 52 can, in some embodiments, preprocess the blood flow sounds to remove noise and then extracts acoustic heart pulses contained within the sounds. The system 52 then processes the extracted acoustic heart pulses using a novel feature extraction and pattern recognition-based machine learning framework to determine whether or not the subject exhibits the biomedical condition. The system 52 can then provide the results to the user.

As is also shown in FIG. 2, the memory 52 can further include a database 54 in which the received pressure signals and the outcomes of the processing can be stored.

Data Preprocessing and Signal Extraction

As noted above, once the blood flow sounds are obtained using the system 10, signal processing techniques can be performed to remove noise from the data and to extract acoustic heart pulses. One such signal processing technique is described in U.S. patent application Ser. No. 15/888,889 ("the '889 application"), filed Feb. 5, 2018. That patent application is incorporated by reference in its entirety into the present disclosure. As described in detail in the '889 application, once the acoustic pressure signal and the acoustic signal are received from the microphones 28 and 34, respectively, noise reduction is performed on the acoustic pressure signal to obtain a signal-to-noise (SNR)-enhanced acoustic pressure signal. In some embodiments, spectral subtraction or adaptive noise cancellation can be used for this purpose.

Once noise cancellation has been performed, source separation can be performed on the SNR-enhanced acoustic pressure signal (i.e., SNR-enhanced $P_{dynamic}$) to extract the acoustic heart pulses. In some embodiments, the source separation comprises wavelet-based source separation. In such a case, discrete wavelet decomposition is performed on the SNR-enhanced acoustic pressure signal to obtain the acoustic heart pulses. In this process, wavelet-based multi-resolution analysis (MRA) is implemented in order to unmask the underlying pulses. In MRA, the given signal $\hat{x}(n)$, i.e., the SNR-enhanced $P_{dynamic}$, is decomposed into various levels of approximation (A) and detail (D) coefficients according to Equation (1).

$$A_m(n) = <\hat{x}(n), \varphi_{mk}(n)>$$

$$D_m(n) = <\hat{x}(n), \psi_{mk}(n)> \quad \text{(Equation 1)}$$

where the < > operator represents inner product, m represents the decomposition level, k represents the translation, ψ represents the mother wavelet with R vanishing moments, and φ corresponds to its scaling function. In order to obtain the approximations and details of the subsequent levels, the wavelet (ψ) and scaling (φ) functions are represented as recursive functions given in Equation (2).

$$\psi(n) = \sum_{p=-\infty}^{\infty} h(p)\varphi(2n-p) \qquad \text{(Equation 2)}$$

$$\varphi(n) = \sum_{p=-\infty}^{\infty} g(p)\varphi(2n-p)$$

In Equation (2), h(p) and g(p) are impulse responses of low pass and high pass quadrature mirror filters, respectively. The approximation and detail coefficients at each level are a result of convolution between the signal (n) with the impulse responses of h(p) and g(p). The approximation coefficients obtained at each level are down sampled by a factor of two and decomposed further into finer approximations and details. This process is continued until all the levels of the MRA are reached. After all the approximation and detail coefficients are obtained from the MRA, level-based hard thresholding is performed by setting the coefficients corresponding to all the scales to zero expect for the coefficients of the interest in a particular level. Using this hard thresholding process, the acoustic heart pulses can be extracted in the wavelet domain.

After application of the hard thresholding, the new coefficients are reconstructed back into the time domain to extract the various signals that make up the SNR-enhanced acoustic pressure signal. Acoustic heart and respiratory signals exhibit different behaviors in the wavelet domain in the sense that acoustic heart signals are highly dynamic and non-stationary, while acoustic respiratory signals are relatively slow varying. Therefore, the chosen mother wavelet ($\psi$) should provide a reasonably good low- and high-frequency resolution to the underlying biological signals of (n) through compact support. In a previous study, the lower cutoff frequency of the pressure field microphone 28 was set to 3.15 Hz. Therefore, any underlying biological signals of interest that contained frequency components below 3.15 Hz would have been attenuated and appeared as discontinuities in the measured pressure data. As a result, the chosen $\psi$ needs to be able to detect the presence of hidden discontinuities. Finally, the $\psi$ should be orthogonal to avoid phase distortions from the transformation.

Feature Extraction and Pattern Recognition

Figure 3:
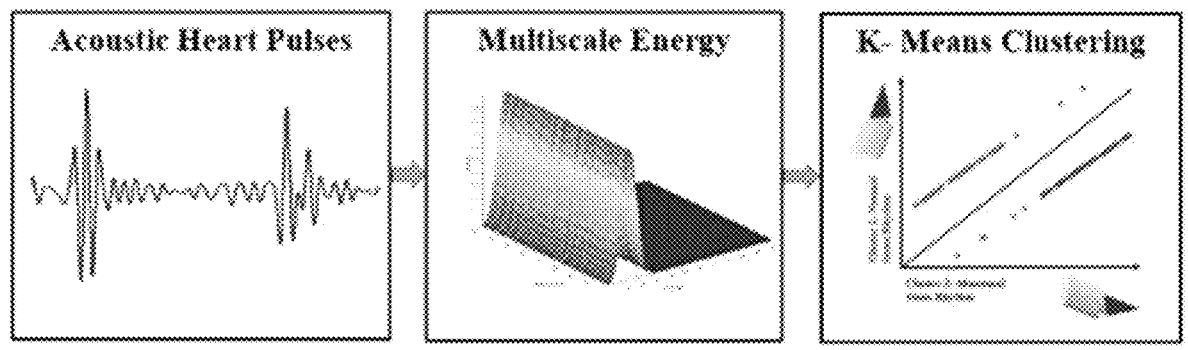
FIG. 3 is a schematic diagram that illustrates an embodiment of an acoustic heart pulse feature extraction and pattern recognition framework.

Once the collected blood flow sounds have been preprocessed and the acoustic heart pulses have been extracted, the extracted acoustic heart pulses are subjected to a feature extraction and pattern recognition framework for sinus rhythm pattern detection. Acoustic heart pulses were extracted from data collected in a previous study conducted by the inventors. The data was collected from the carotid artery of an animal (pig) model corresponding to normal and abnormal sinus rhythms using a system similar to the system 10 shown in FIG. 1. The developed framework initially segments the data, extracts the features, and recognizes the pattern from the extracted features. Through experiments performed in a recent study, it was determined that the implemented feature extraction and pattern recognition framework is able to independently cluster normal and abnormal sinus rhythm patterns of the acoustic heart pulses. FIG. 3 is schematic diagram that illustrates an overview of the signal analysis and processing framework, which is described below.

Computation of Multiscale Energy (MSE) Features

Prior to feature extraction, the extracted acoustic heart pulses are segmented into multiple time segments. A continuous time wavelet transform (CTWT)-based feature, referred to herein as the "multiscale energy" (MSE) feature was developed and is computed for each segment of the acoustic heart pulse. The CTWT of a bioacoustic signal provides different information and noise at various spatial scales. Analysis is significantly improved by viewing the signal at multiple resolutions, especially when the information of interest is present in only few scale levels.

The normalized CTWT provides both good frequency and time (or space) localization and indicates when and where each frequency component occurs for the signal. The MSE feature is then computed using a Coiflet mother wavelet. When a time domain signal is subjected to the CTWT, the result is a time frequency characterization of the signal at different scales at a given time. The absolute summation of the characterized scale coefficient corresponding to every time index results in multiscale energy. The normalized CTWT of a continuous signal h(t) is given by Equation (3):

$$W_{h;\psi}(\tau, s) = \frac{1}{\sqrt{s}} \int_{-\infty}^{\infty} h(t) * \left(\frac{t-\tau}{s}\right) dt \qquad (3)$$

where W is the computed continuous wavelet transform, h(t) is a segment of the acoustic heart pulse, s is a scale coefficient associated with stretching or compressing of the signal in time, $\tau$ is a translation parameter, and $\psi$ is a chosen mother wavelet. The MSE is then computed using Equation (4):

$$MSE(s) = \Sigma_\tau |W_{h;\psi}(\tau,s)|^2 \qquad (4)$$

The MSE feature is computed at each scale of the CTWT of h(t) using a Coiflet wavelet with four vanishing moments as the chosen mother wavelet, $\psi$. In essence, the mother wavelet stretches and compresses the time domain signal. The magnitude of how much the signal is either stretched or compressed is defined by a parameter called "scale." Thus, scale corresponds to the pseudo-frequency component of the mother wavelet.

K-Means Clustering

In the next phase of the processing, K-means, a hard clustering algorithm, is applied to the computed MSE features of the acoustic heart pulse segments for sinus rhythm pattern recognition. The following procedure can be used to cluster the MSE features:

1. The computed MSE feature vector set (v) of the extracted acoustic heart pulses with dimensions $n_p \times f_p$ is input into the algorithm. Here, $n_p$ is the number of instances and $f_p$ represents number of features.
2. Initial cluster centers are randomly selected from the feature set $n_p \times f_p$.
3. Features that are closest to the cluster centroids according to the Euclidean distance function shown in Equation (5) (below) are assigned to the cluster number (j) depending on the maximum number of clusters (K) and $n_p$.

$$\Sigma_{j=1}^{K} \Sigma_{p=1}^{n_p} \|v_p^j - c_j\|^2 \qquad (5)$$

4. Based on the newly formed clusters, the centroids are recomputed.
5. Steps 2, 3, and 4 are then iteratively repeated until the Euclidean distance function reaches convergence.

Experimental Results

Figure 4A:
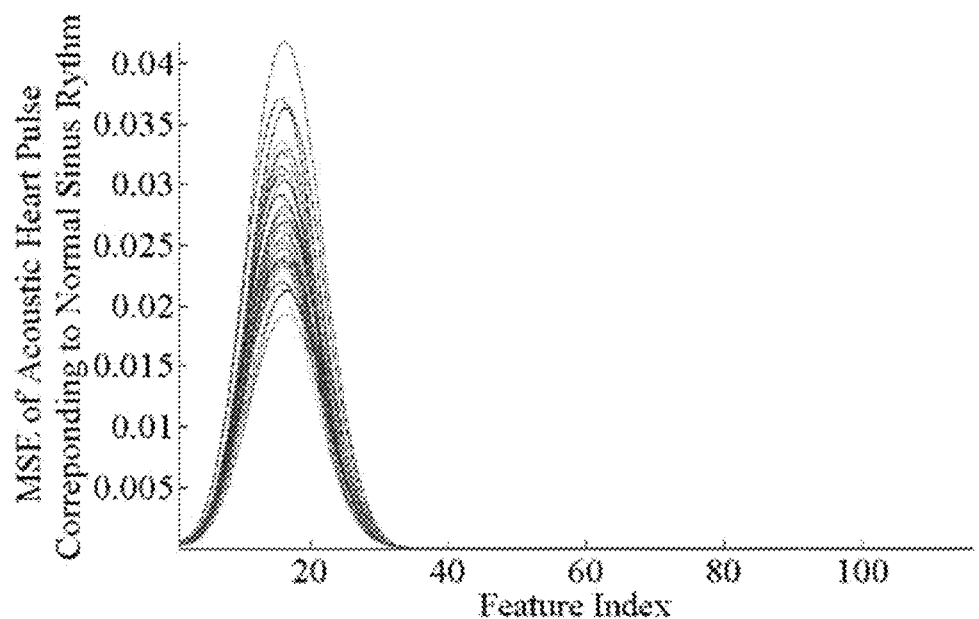
FIG. 4A is a graph that shows multiscale energy (MSE) features of an acoustic heart pulse corresponding to a normal sinus rhythm.
Figure 4B:
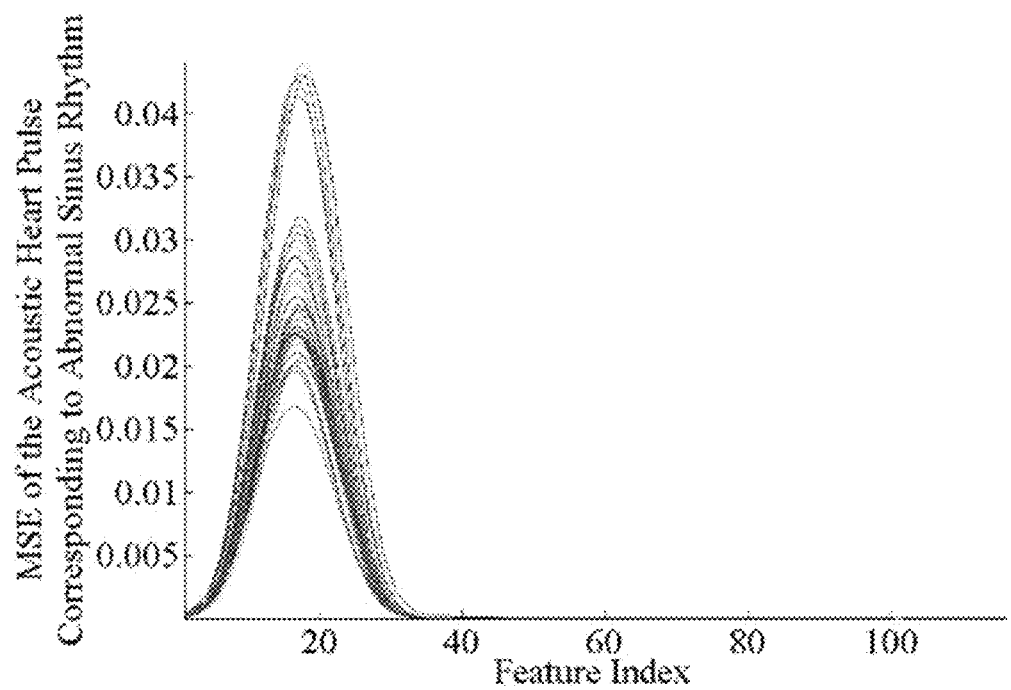
FIG. 4B is a graph that shows MSE features of an acoustic heart pulse corresponding to an abnormal sinus rhythm.

Acoustic heart pulses corresponding to the normal and abnormal sinus rhythms from the previous animal model study were processed by extracting the MSE features and then subjecting them to K-means clustering for pattern recognition. The acoustic heart pulses were first segmented into 3 second long frames and then the MSE features were computed for each frame of the acoustic heart pulse. The number of frame instances $n_p$ and the number of features $f_p$ for the MSE feature set was 80×116, where 80 is number of frames corresponding to acoustic heart pulses of both the normal and abnormal sinus rhythms and 116 is the number features computed based on the scale vector of the CTWT. FIGS. 4A and 4B show the MSE features computed for the acoustic heart pulses corresponding to normal and abnormal sinus rhythms.

The computed MSE features were scaled and separated into 2 clusters using a Euclidean distance-based K-means clustering algorithm. The cluster number (K) was selected based on the average silhouette coefficient ($C_p$) computation. The $C_p$ for the data used in the experiments was determined to be 2, which can be associated to clusters belonging to normal and abnormal sinus rhythms.

Figure 5:
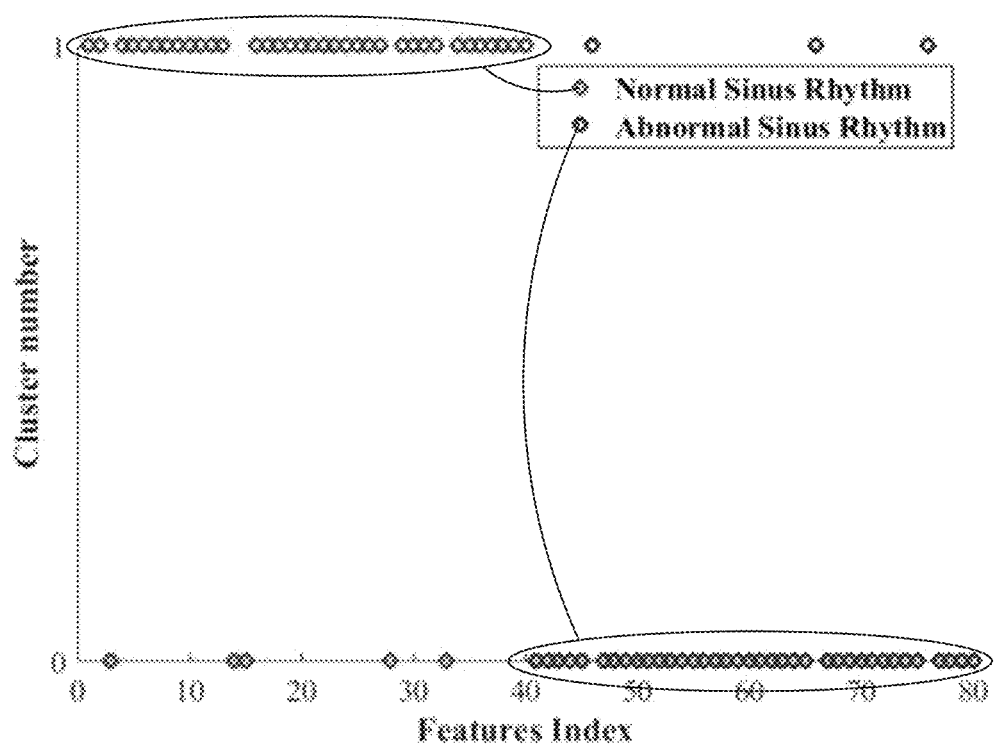
FIG. 5 is a graph that shows the results of K-Means clustering of the normal and abnormal MSE features.

FIG. 5 shows the qualitative results of the K-means clustering. It can be qualitatively observed from this figure that K-means clustering provides a satisfactory sinus rhythm pattern recognition by separating the MSE features into two different clusters ("normal" and "abnormal"). To further validate the developed MSE features and the pattern recognition framework, quantitative factors, such as sensitivity, specificity, and accuracy were computed. Table 1 presents the results of confusion matrix of the cluster analysis.

TABLE 1

Confusion Matrix of the Cluster Analysis.

| np = 80 | Predicted: No | Predicted: Yes |
|---|---|---|
| Actual: No | TN = 37 | FP = 3 |

The confusion matrix shown in Table 1 was computed for 80 feature instances. The feature instances corresponding to the normal sinus rhythm were defined as actual: Yes. The abnormal sinus rhythm were defined as actual: No. Sensitivity and specificity were computed from Table 1 to show that the developed framework recognizes the patterns of the normal sinus rhythm with 87.5% precision and abnormal sinus rhythm with 92.5% precision. In addition, it was also noted that the overall ability of the developed framework in recognizing the patterns of the sinus rhythms was accurate to 90%, which is a vast improvement over current techniques.

Example Embodiment

Figure 6:
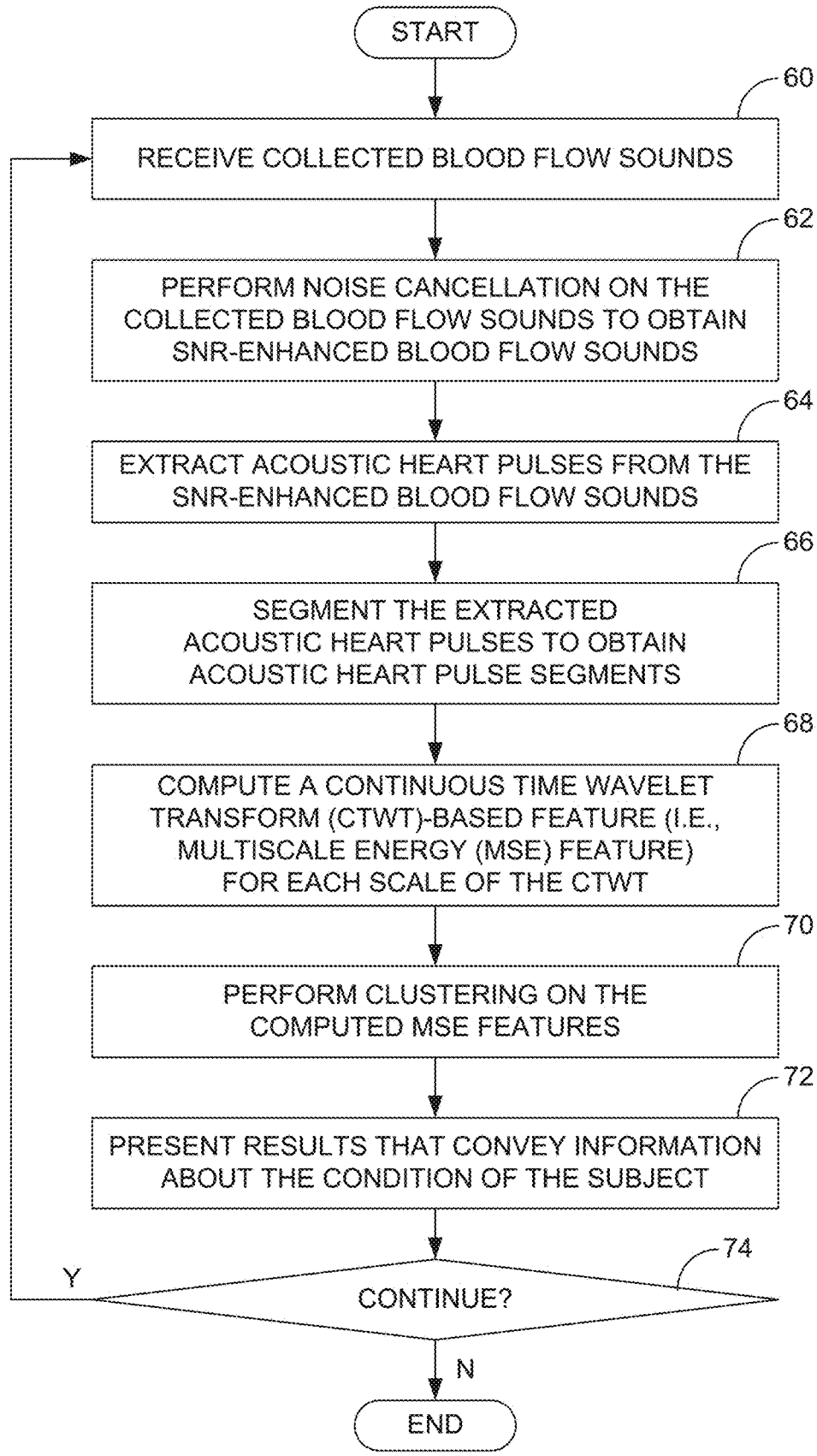
FIG. 6 is a flow diagram that illustrates an embodiment of a method for identifying a biomedical condition that uses feature extraction and pattern recognition.

FIG. 6 is a flow diagram that summarizes an embodiment of identifying a biomedical condition, specifically arrhythmia, using the signal feature extraction and pattern recognition described above. In some embodiments, this method can be performed by the biosignal processing system 52 executed by the computing device 32 (see FIGS. 1 and 2).

Beginning with block 60 of FIG. 6, the collected blow flow sounds are received. As described above, the blood flow sounds can, in some embodiments, be collected using an acoustic catheter stethoscope, such as that shown in FIG. 1. With reference to block 62, noise cancellation is performed on the collected blood flow sounds to obtain SNR-enhanced blood flow sounds. In some embodiments, the noise cancellation can comprise spectral subtraction or adaptive noise cancellation. Next, acoustic heart pulses are extracted from the SNR-enhanced blood flow sounds, as indicated in block 64. In some embodiments, the acoustic heart pulses are extracted by performing wavelet-based source separation.

At this point, the acoustic heart pulses are segmented to obtain acoustic heart pulse segments, as indicated in block 66. The segments are time segments and, as described above, can be on the order of a few seconds long each. Next, with reference to block 68, a CTWT-based feature, i.e., an MSE feature, is computed for each scale of the CTWT. In some embodiments, the MSE features are calculated using Equation (4) identified above using a Coiflet wavelet with four vanishing moments as the chosen mother wavelet.

Referring next to block 70, once the MSE features have been computed, clustering is performed on the MSE features to classify the features and, therefore, the subject's heart activity. In the present example, the heart activity at issue is the subject's heart rhythm, which is either classified as being normal or abnormal (i.e., arrhythmia). In some embodiments, the clustering can comprise K-means clustering that is achieved by performing steps 1-5 identified above.

At this point, the subject's heart activity has been classified and results that convey information about the subject's condition can be presented to a user, as indicated in block 72. In keeping with the current example, the results can be a graphical indication of where the subject's heart activity falls, i.e., within or outside of the normal range. In other embodiments, the results can simply be presented as a positive or a negative indication of arrhythmia. With reference next to decision block 74, flow can either return to block 60 and the entire process can be repeated, or the session can be terminated.

CONCLUSIONS

In the above disclosure, a feature extraction and pattern recognition framework for biomedical acoustic signals has been described and a comprehensive description of the developed framework has been provided. The implemented feature extraction technique uses a novel time-frequency energy computation to represent the acoustic heart pulses. Then, the computed features are processed using a K-means clustering algorithm to recognize the patterns of the normal and abnormal sinus rhythms. Finally, the developed framework was qualitatively and quantitatively validated. The validation results show that the developed framework recognizes the patterns of the sinus rhythms with an accuracy rate of 90%. While this is a great improvement over current techniques, even greater accuracy may be possible by using a multimodal framework that includes information from other vital biosignals, such as other biosignals acquired by the acoustic catheter stethoscope.

The invention claimed is:
1. A method for identifying a biomedical condition of a subject, the method comprising:
receiving collected blood flow sounds;
extracting acoustic heart pulses from the collected blood flow sounds;
segmenting the acoustic heart pulses to obtain acoustic heart pulse segments;
computing a continuous time wavelet transform-based feature for each acoustic heart pulse segment by computing a multiscale energy (MSE) feature for each acoustic heart pulse segment; and performing clustering on the computed continuous time wavelet transform-based features to determine whether or not the subject is experiencing the biomedical condition;

outputting a result to an individual, to convey whether or not the subject is experiencing the biomedical condition.

2. The method of claim 1, wherein extracting acoustic heart pulses comprises performing wavelet-based source separation on the collected blood flow sounds.

3. The method of claim 1, wherein segmenting comprises segmenting the acoustic heart pulses into time segments.

4. The method of claim 1, wherein computing the MSE features comprises using the following equation:

$$MSE(s) = \Sigma_\tau |W_{h;\psi}(\tau,s)|^2$$

where W is the computed continuous wavelet transform, h is the segment of the acoustic heart pulse, s is a scale coefficient associated with stretching or compressing of a signal in time, $\tau$ is a translation parameter, and $\psi$ is a chosen mother wavelet.

5. The method of claim 1, wherein computing the MSE features comprises computing an MSE feature for each scale of the continuous time wavelet transform.

6. The method of claim 5, wherein computing an MSE feature for each scale comprises computing an MSE feature for each scale of the continuous time wavelet transform using a Coiflet wavelet as the chosen mother wavelet.

7. The method of claim 1, wherein performing clustering comprises performing K-means clustering.

8. The method of claim 1, further comprising cancelling noise from the collected blood flow sounds before extracting the acoustic blood pulses.

9. A system for identifying a biomedical condition of a subject, the system comprising:
a computing device having a processor and a memory, the memory storing computer-executable instructions that when executed by the processor, cause the computing device to:
receive collected blood flow sounds;
extract acoustic heart pulses from the collected blood flow sounds;
segment the acoustic heart pulses to obtain acoustic heart pulse segments;
compute a continuous time wavelet transform-based feature for each acoustic heart pulse segment by computing a multiscale energy (MSE) feature for each acoustic heart pulse segment; and
perform clustering on the computed continuous time wavelet transform-based features to determine whether or not the subject is experiencing the biomedical condition;
output a result to a user, to convey whether or not the subject is experiencing the biomedical condition.

10. The system of claim 9, wherein extracting acoustic heart pulses comprises performing wavelet-based source separation on the collected blood flow sounds.

11. The system of claim 9, wherein segmenting comprises segmenting the acoustic heart pulses into time segments.

12. The system of claim 9, wherein computing the MSE features comprises using the following equation:

$$MSE(s) = \Sigma_\tau |W_{h;\psi}(\tau,s)|^2 \qquad (4)$$

where W is the computed continuous wavelet transform, h is the segment of the acoustic heart pulse, s is a scale coefficient associated with stretching or compressing of a signal in time, $\tau$ is a translation parameter, and $\psi$ is a chosen mother wavelet.

13. The system of claim 9, wherein computing the MSE features comprises computing an MSE feature for each scale of the continuous time wavelet transform.

14. The system of claim 13, wherein computing an MSE feature for each scale comprises computing an MSE feature for each scale of the continuous time wavelet transform using a Coiflet wavelet as the chosen mother wavelet.

15. The system of claim 9, wherein performing clustering comprises performing K-means clustering.

16. The system of claim 9, wherein the computing device is further configured to cancel noise from the collected blood flow sounds before extracting the acoustic blood pulses.

* * * * *